United States Patent
Guo et al.

(10) Patent No.: US 10,893,233 B1
(45) Date of Patent: Jan. 12, 2021

(54) INTERACTION METHOD, INTERACTION DEVICE AND INTERACTION SYSTEM FOR REMOTE CONSULTATION

(71) Applicant: BOE TECHNOLOGY GROUP CO., LTD., Beijing (CN)

(72) Inventors: Xiaoqin Guo, Beijing (CN); Jingyu Zhang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 16/916,919

(22) Filed: Jun. 30, 2020

(30) Foreign Application Priority Data

Sep. 27, 2019 (CN) .......................... 2019 1 0927903

(51) Int. Cl.
| | |
|---|---|
| H04N 7/14 | (2006.01) |
| H04L 9/32 | (2006.01) |
| H04L 29/06 | (2006.01) |
| G16H 80/00 | (2018.01) |

(52) U.S. Cl.
CPC ............ *H04N 7/147* (2013.01); *G16H 80/00* (2018.01); *H04L 9/3213* (2013.01); *H04L 69/161* (2013.01)

(58) Field of Classification Search
CPC . H04N 7/14; H04N 7/15; H04L 29/06; H04L 9/32
USPC ................................. 348/14.01–14.16; 705/2
See application file for complete search history.

(56) References Cited

U.S. PATENT DOCUMENTS

| | | | | |
|---|---|---|---|---|
| 2014/0200913 A1* | 7/2014 | Budhrani | ............... | G06Q 10/10 705/2 |
| 2019/0237204 A1* | 8/2019 | Huang | .................. | H04N 7/155 |

\* cited by examiner

*Primary Examiner* — Melur Ramakrishnaiah
(74) *Attorney, Agent, or Firm* — Brooks Kushman P.C.

(57) ABSTRACT

An interaction method, an interaction device and an interaction system for remote consultation are provided. The interaction method includes: acquiring a remote consultation request; creating a consultation group based on a real-time audio and video cloud service interface, and recording the remote consultation request in a database; generating a consultation token based on patient information in the remote consultation request in the database and attribute information of the consultation group, and recording the consultation token in the database; and sending the consultation token in the database to a first terminal and a second terminal, and performing an information interaction by the first terminal and the second terminal based on a user datagram protocol in response to the first terminal and the second terminal entering the consultation group according to the consultation token.

15 Claims, 3 Drawing Sheets

INTERACTION METHOD, INTERACTION DEVICE AND INTERACTION SYSTEM FOR REMOTE CONSULTATION

CROSS REFERENCE OF RELATED APPLICATION

This application claims priority to Chinese Patent Application No. 201910927903.7 filed on Sep. 27, 2019, which is incorporated herein by reference in its entirety.

TECHNICAL FIELD

The present disclosure relates to field of medical technology. Specifically, the present disclosure relates to an interaction method, an interaction device and an interaction system for remote consultation.

BACKGROUND

Health is always an important issue that people pay attention to. People in large hospitals are often overcrowded, and patients often have long queues when they are in pain. They can only see doctors through complicated procedures. On the other hand, the patient's condition is very different, and some non-critical conditions are also involved in the consultation process, resulting in low efficiency of doctors' consultations, which further leads to difficulties in seeing a doctor.

Based on the development of network communication, the concept of remote consultation gradually changed from theory to reality. However, due to the complexity of the network environment and the increasing volume of high-definition audio and video data, most of the interaction systems on the market for remote consultation use low-resolution audio and video technology to perform a communication between patients and doctors. Because the quality of audio and video is poor, it is difficult to achieve the accuracy, real-time and safety of remote consultation information transmission, so even the interaction system used for remote consultation cannot well reflect the appearance of the lesion and the physical condition of the patient. Therefore, it is difficult for the remote consultation to be fully and smoothly applied.

SUMMARY

An interaction method for remote consultation is provided in the present disclosure, including:
acquiring a remote consultation request;
creating a consultation group based on a real-time audio and video cloud service interface, and recording the remote consultation request in a database;
generating a consultation token based on patient information in the remote consultation request in the database and attribute information of the consultation group, and recording the consultation token in the database; and
sending the consultation token in the database to a first terminal and a second terminal, and performing an information interaction by the first terminal and the second terminal based on a user datagram protocol in response to the first terminal and the second terminal entering the consultation group according to the consultation token.

Optionally, the acquiring the remote consultation request includes:
acquiring the remote consultation request which is based on the user datagram protocol; and
the sending the consultation token in the database to the first terminal and the second terminal includes:
sending the consultation token to the first terminal and the second terminal based on the user datagram protocol.

Optionally, the performing the information interaction by the first terminal and the second terminal based on the user datagram protocol in response to the first terminal and the second terminal entering the consultation group according to the consultation token includes:
generating a connection success notification in response to the first terminal and the second terminal entering the consultation group according to the consultation token;
sending the connection success notification to the first terminal and the second terminal;
acquiring audio and video stream information pushed by the first terminal; and
sending the audio and video stream information to the second terminal, based on the real-time audio and video cloud service interface and the user datagram protocol.

Optionally, the acquiring the audio and video stream information pushed by the first terminal includes:
acquiring the audio and video stream information which is encoded, compressed and pushed by the first terminal; and
the sending the audio and video stream information to the second terminal based on the real-time audio and video cloud service interface and the user datagram protocol includes:
sending, to the second terminal, the audio and video stream information which is encoded, compressed and pushed, to enable the second terminal to decode and display the audio and video stream information which is encoded, compressed and pushed.

Optionally, the user datagram protocol includes a service quality policy and a packet loss compensation method, the packet loss compensation method adopts a packet loss retransmission;
the patient information includes at least one of patient identification information and registration information;
the attribute information of the consultation group includes at least one of business application account information, a consultation group name or a consultation group service type.

Optionally, the registration information includes: a consultation order, registration section information, and the business application account information include consultation business type information.

Optionally, the first terminal is a terminal of a patient, and the second terminal is a terminal of a doctor;
where the second terminal includes a plurality of sub terminals, and each of the sub terminals corresponds to a doctor;
the sending the audio and video stream information to the second terminal based on the real-time audio and video cloud service interface and the user datagram protocol includes:
sending the audio and video stream information to the sub terminals of the second terminal based on the real-time audio and video cloud service interface and the user datagram protocol, to enable the patient to exchange information with a plurality of doctors.

An interaction device for remote consultation is further provided in the present disclosure, including a processor, a memory and a program, where the processor executes the program to:

acquire a remote consultation request;

create a consultation group based on a real-time audio and video cloud service interface, and record the remote consultation request in a database;

generate a consultation token based on patient information in the remote consultation request in the database and attribute information of the consultation group, and record the consultation token in the database; and send the consultation token in the database to a first terminal and a second terminal, and perform an information interaction of the first terminal and the second terminal based on a user datagram protocol in response to the first terminal and the second terminal entering the consultation group according to the consultation token.

Optionally, the processor executes the program to acquire the remote consultation request which is based on the user datagram protocol;

where the processor executes the program to send the consultation token to the first terminal and the second terminal based on the user datagram protocol.

Optionally, the processor executes the program to:

generate a connection success notification in response to the first terminal and the second terminal entering the consultation group according to the consultation token;

send the connection success notification to the first terminal and the second terminal;

acquire audio and video stream information pushed by the first terminal; and send the audio and video stream information to the second terminal, based on the real-time audio and video cloud service interface and the user datagram protocol.

Optionally, the processor executes the program to acquire the audio and video stream information which is encoded, compressed and pushed by the first terminal;

where the processor executes the program to send, to the second terminal, the audio and video stream information which is encoded, compressed and pushed, to enable the second terminal to decode and display the audio and video stream information which is encoded, compressed and pushed.

Optionally, the user datagram protocol includes a service quality policy and a packet loss compensation method, the packet loss compensation method adopts a packet loss retransmission;

the patient information includes at least one of patient identification information and registration information;

the attribute information of the consultation group includes at least one of business application account information, a name of the consultation group or a service type of the consultation group.

Optionally, the registration information includes: a consultation order, registration section information, and the business application account information include consultation business type information.

An interaction system for remote consultation is further provided in the present disclosure, including a remote management server, a remote consultation control device, a first terminal and a second terminal;

the remote consultation control device is configured to send a remote consultation request to the remote management server;

the remote management server includes a real-time audio and video cloud service interface and is configured to:

create a consultation group based on a real-time audio and video cloud service interface and the remote consultation request, and record the remote consultation request in a database;

generate a consultation token based on patient information in the remote consultation request in the database and the attribute information of the consultation group, and record the consultation token in the database;

the first terminal and the second terminal are configured to receive the consultation token sent by the remote management server, enter the consultation group based on the consultation token, and exchange information based on a user datagram protocol.

Optionally, both the first terminal and the second terminal include an audio and video acquiring and codec circuit;

the audio and video acquiring and codec circuit is configured to encode and compress an audio and video stream acquired by the first terminal or the second terminal, and decode audio and video stream information sent by the remote management server.

BRIEF DESCRIPTION OF THE DRAWINGS

In order to more clearly explain the technical solutions in the embodiments of the present disclosure, the drawings used in the description of the embodiments of the present disclosure will be briefly introduced below.

DETAILED DESCRIPTION

Figure 1:
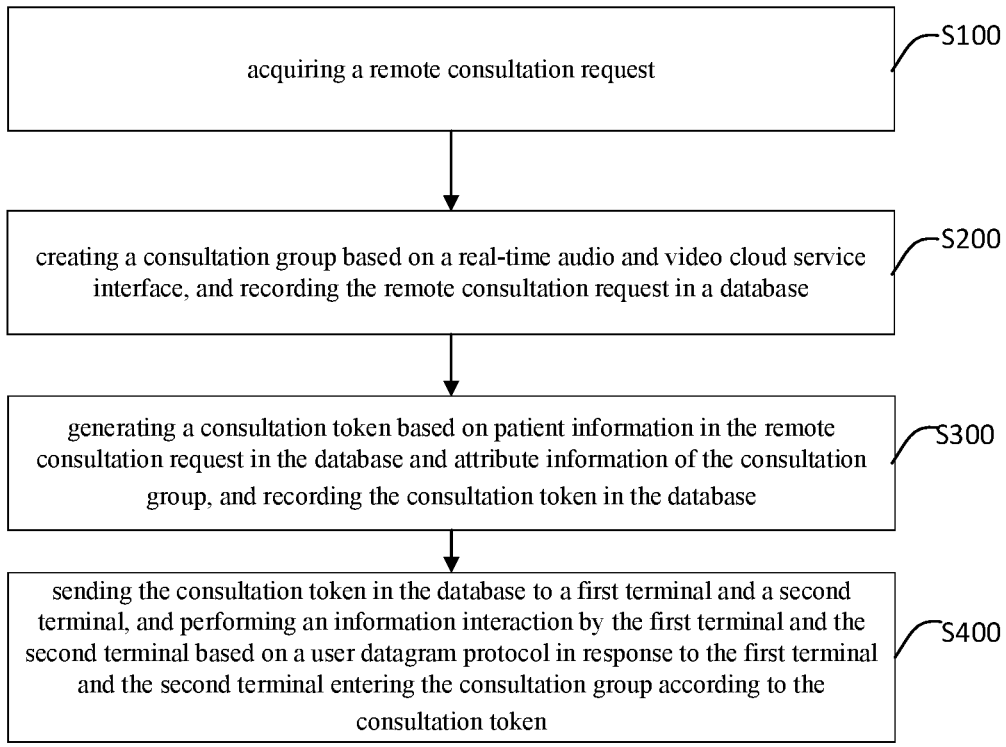
FIG. 1 is a flow chart of an interaction method for remote consultation in an embodiment of the present disclosure.

The embodiments of the present disclosure are described in detail below. Examples of the embodiments are shown in the drawings, in which the same or similar reference numerals denote the same or similar elements or elements having the same or similar functions. The embodiments described below with reference to the drawings are exemplary, and are only used to explain the present disclosure, and is construed as limiting the present disclosure.

Those skilled in the art can understand that unless specifically stated, the singular forms "a", "an", "said" and "the" used herein may also include the plural forms. It should be further understood that the word "comprising" used in the description of the present disclosure refers to the presence of the described features, integers, steps, operations, elements and/or components, but does not exclude the presence or addition of one or more other features, Integers, steps, operations, elements, components, and/or their groups. It should be understood that when an element is referred to as being "connected" or "coupled" to another element, it can be directly connected or coupled to the other element, or intervening elements may also be present. In addition, "connected" or "coupled" as used herein may include wirelessly connected or wirelessly coupled. The word "and/or" used herein includes all or any unit and all combinations of one or more associated listed items.

To make the objectives, technical solutions, and advantages of the present disclosure clearer, the following describes the embodiments of the present disclosure in further detail with reference to the drawings.

Under the situation of seeing a doctor, it is important for the patient to talk to the doctor to tell the state of illness. However, the current medical resources of large hospitals are limited, and the continuous flow of patients makes the contact between the patient and the doctor too short, which is not conducive to understanding the state of illness and comforting the patient's mood. The method of remote consultation can eliminate the restrictions on places for medical treatment and greatly increase the time for real consultation. However, the remote consultation in the related art cannot yet realize the transmission of real-time audio and video data, and thus it cannot truly realize the practical remote consultation service, which hinders the development of the remote consultation service. The transmission of audio and video data cannot be achieved. On the one hand, the network is unstable, which easily affects the stability of the transmission of audio and video information, causing transmission delays. On the other hand, the audio and video server software and hardware services of medical institutions in the related art have high cost and low resource use ratio, the related services cannot be automatically expanded, the device is closed to the outside, the scalability is poor, and may not be able to effectively access the Internet. The above technical issues make the remote consultation not widely used.

An interaction method, an interaction device and an interaction system for remote consultation are provided in some embodiments of the present disclosure, to solve the above technical issues in the related art.

The technical solutions of the present disclosure and how the technical solutions of the present disclosure solve the above technical issues will be described in detail below with specific embodiments. The following embodiments may be combined with each other, and the same or similar concepts or processes may not be repeated in some embodiments. The embodiments of the present disclosure will be described below with reference to the drawings.

Generally speaking, the interaction system used for remote consultation includes a remote consultation control device, a remote management server, and a remote consultation terminal, all of which are connected via the Internet. For example, the remote consultation control device is equivalent to the registration medical equipment in the medical institution, the remote management server is responsible for managing all medical information in the medical institution, including a database for storing a large amount of data, and the remote consultation terminal is equivalent to the computer terminal of the patient or doctor which are specifically named as the first terminal and the second terminal.

For example, the first terminal may represent a computer terminal of a patient, and the second terminal may represent a computer terminal of a doctor. In addition to the first terminal and the second terminal, other terminals may even exist. At the same time, there may be one or more first terminals and second terminals. After the consultation token is sent to the first terminal and the second terminal, the first terminal and the second terminal with the specific consultation token can accurately enter the consultation group corresponding to the consultation token. With the support of relevant network communication protocols, information transmission and data exchange between the first terminal and the second terminal are realized.

For example, the second terminal represents a computer terminal of a doctor, which includes a plurality of sub terminals, and each of the sub terminals corresponds to a doctor. When the patient needs to perform a remote consultation with a plurality of doctors and the consultation token is sent to the first terminal of the patient and the sub terminals of the doctors, the first terminal of the patient and sub terminals of the second terminal of the doctor with the specific consultation token can accurately enter the consultation group corresponding to the consultation token, so as to enable the patient to perform a remote consultation with a plurality of doctors.

An interaction method for remote consultation is provided in an embodiment of the present disclosure. As shown in FIG. 1, the method includes:

S100: acquiring a remote consultation request.

S200: creating a consultation group based on a real-time audio and video cloud service interface, and recording the remote consultation request in a database.

Optionally, when the remote management server acquires the remote consultation request, a consultation group is created based on the real-time audio and video cloud service interface.

Real-time audio and video cloud service is a type of cloud service. Cloud service refers to obtaining required services in an on-demand and easily scalable manner through the network. For example, the audio and video cloud services are used to receive, process, and transmit audio and video data. Cloud services enable users to switch resources to required applications and access computers and storage systems based on demand by distributing service computing on a large number of distributed computers instead of local computers or remote servers. The user equipment is connected to the real-time audio and video cloud service through the network interface, and the real-time audio and video cloud service provides special services, which can automatically expand the user equipment and system and transfer the advantages of the audio and video cloud service. The user equipment and system may be an independent computer system, or a local area network formed by connecting many independent computers by a server, such as a computer system in a hospital. For the specific user equipment and system and the connection method of the audio and video cloud service, those skilled in the related art can understand, and will not be repeated herein.

Through the special service provided by the real-time audio and video cloud service, it is able to create a consultation group for remote consultation, build a communication platform between doctors and patients. Specifically, it is equivalent to constructing a virtual call room on the communication platform, to prepare audio and video data for transmission during the consultation.

S300: generating a consultation token based on patient information in the remote consultation request in the database and attribute information of the consultation group, and recording the consultation token in the database.

Optionally, the remote management server generates a consultation token based on the patient information in the remote consultation request and the attribute information of the consultation group created based on the real-time audio and video cloud service interface.

Token represents the right to perform certain operations. According to the remote consultation request, a communication secret with the authorization to execute the consultation communication operation is generated, so that a specific object can be connected to a specific communication contact platform according to the consultation token, such as entering a consultation group established through S100.

In a specific embodiment, the patient information includes at least one of patient identification information and registration information; the attribute information of the consultation group includes at least one of business application account information, a consultation group name or a consultation group service type. For example, the patient's identity information includes the patient's age, gender, and even occupational information. The registration information includes the consultation order, the registration section, and even the past medical records. The business application account information includes information about the type of consultation business, such as the ophthalmology clinic account, internal medicine clinic account, etc.

S400: sending the consultation token in the database to a first terminal and a second terminal, and performing an information interaction by the first terminal and the second terminal based on a user datagram protocol in response to the first terminal and the second terminal entering the consultation group according to the consultation token.

Optionally, the remote management server sends the consultation token in the data base to the first terminal and the second terminal, and then the first terminal and the second terminal perform an information interaction based on a user datagram protocol in response to the first terminal and the second terminal entering the consultation group according to the consultation token.

For example, the first terminal may represent a computer terminal of a patient, and the second terminal may represent a computer terminal of a doctor. In addition to the first terminal and the second terminal, other terminals may even exist. At the same time, there may be one or more first terminals and second terminals. After the consultation token is sent to the first terminal and the second terminal, the first terminal and the second terminal with the specific consultation token can accurately enter the consultation group corresponding to the consultation token. With the support of relevant network communication protocols, information transmission and data exchange between the first terminal and the second terminal are realized.

User Datagram Protocol (UDP) is a simple transport layer protocol for connectionless and unreliable datagrams. The protocol does not need to establish a connection before sending data, and there is no connection to release at the end of sending data. Therefore, the network resource overhead and the delay before sending data are reduced, so the low latency of audio and video data transmission can be ensured and real-time communication of remote consultation can be realized.

The interaction method for remote consultation provided by the present disclosure is based on the real-time audio and video cloud service interface to create a consultation group, to achieve multi-terminal information interaction based on the user datagram protocol, and the real-time audio and video cloud service may automatically allocate the optimal and smoothest transmission path in real time according to the network transmission status and load status, the user datagram protocol has a low latency, thereby ensuring a real-time interaction with high-definition audio and video during the remote consultation process, effectively promoting the realization of remote consultation.

In some embodiments of the present disclosure, the acquiring the remote consultation request includes: acquiring the remote consultation request which is based on the user datagram protocol. The sending the consultation token in the database to the first terminal and the second terminal includes: sending the consultation token to the first terminal and the second terminal based on the user datagram protocol. That is, the acquiring the remote consultation request and the sending the consultation token to the first terminal and the second terminal are based on the user datagram protocol. According to the characteristics of the user datagram protocol described above, it is able to further ensure the low latency of the communication line of the remote consultation and the communication efficiency of the real-time audio and video communication of the remote consultation.

In some embodiments of the present disclosure, the user datagram protocol includes a service quality policy and a packet loss compensation method, the packet loss compensation method adopts a packet loss retransmission. Although the user datagram protocol has the characteristics of low latency and high transmission rate, the transmission reliability is lower than that of Transmission Control Protocol/Internet Protocol (TCP/IP). In order to improve the network transmission reliability of user datagram protocol, a layer of link Quality of Service (QoS) monitoring and packet loss compensation on UDP can ensure the reliable arrival of UDP transmission. For packet loss compensation method, it usually consists of message redundancy, Forward Error Correction (FEC) and packet loss retransmission, where packet loss retransmission can be retransmitted on demand, which is more suitable for real-time video transmission application scenarios.

Figure 2:
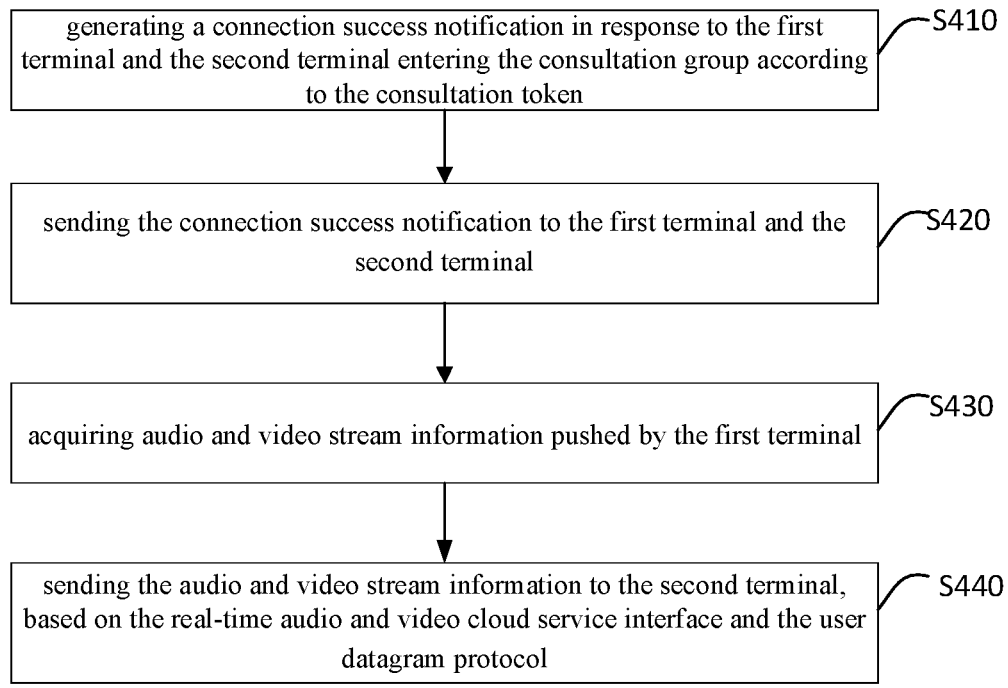
FIG. 2 is a flow chart of Step 300 in an embodiment of the present disclosure.

In some embodiments of the present disclosure, as shown in FIG. 2, the performing the information interaction by the first terminal and the second terminal based on the user datagram protocol in response to the first terminal and the second terminal entering the consultation group according to the consultation token includes:

S410: generating a connection success notification in response to the first terminal and the second terminal entering the consultation group according to the consultation token.

Optionally, the remote server generates a connection success notification in response to the first terminal and the second terminal entering the consultation group according to the consultation token S420: sending the connection success notification to the first terminal and the second terminal.

Optionally, the remote management server sends the connection success notification to the first terminal and the second terminal. When both the first terminal and the second terminal enter the consultation group, it is indicated that the connection between the first terminal and the second terminal is achieved, a notification of successful connection of the first terminal may be sent to the second terminal, and a notification of successful connection of the second terminal may be sent to the first terminal.

S430: acquiring audio and video stream information pushed by the first terminal.

When both the first terminal and the second terminal enter the consultation group, the first terminal and the second terminal can realize information interconnection through the remote management server. Both the first terminal and the second terminal have the information collection function. The first terminal collects audio and video stream information, and the first terminal pushes the collected audio and video stream information to the remote management server. For the second terminal, it can also do the same. The audio and video stream information is usually the patient's image and sound, or the doctor's image and sound.

Optionally, after the first terminal or the second terminal receives the connection success notification, the remote management server acquires the audio and video stream information transmitted by the first terminal or the second terminal and transmitted based on the user datagram protocol.

S440: sending the audio and video stream information to the second terminal, based on the real-time audio and video cloud service interface and the user datagram protocol.

When the remote management server obtains the audio and video stream information pushed by the first terminal, the audio and video stream information is sent to the second terminal, and if the remote server obtains the audio and video stream information pushed by the second terminal, the audio and video stream information is sent to the first terminal, so as to implement information interaction between the first terminal and the second terminal.

Optionally, based on the real-time audio and video cloud service interface, the remote management server sends the audio and video stream information pushed based on the user datagram protocol to the second terminal.

In some embodiments of the present disclosure, the acquiring the audio and video stream information pushed by the first terminal includes: acquiring the audio and video stream information which is encoded, compressed and pushed by the first terminal. That is, the audio and video stream information acquired by the remote management server is encoded and compressed.

In addition, the sending the audio and video stream information to the second terminal based on the real-time audio and video cloud service interface and the user datagram protocol includes: sending, to the second terminal, the audio and video stream information which is encoded, compressed and pushed, to enable the second terminal to decode and display the audio and video stream information which is encoded, compressed and pushed. Optionally, the remote management server packages and encapsulates the acquired, encoded and compressed audio and video stream information according to the user datagram protocol to obtain a data package containing the encoded and compressed audio and video stream information based on the user datagram protocol. The data packet containing the encoded and compressed audio and video stream information is sent to the second terminal through the real-time audio and video cloud service interface, so that the second terminal analyzes the data packet containing the encoded audio and video stream information based on user datagram protocol, to obtain the compressed audio and video stream information packet, and decodes and displays the encoded and compressed audio and video stream information.

By encoding and compressing the audio and video stream information transmitted to the real-time audio and video cloud service, the occupancy rate of the audio and video stream information transmission on network resources can be reduced, and the transmission efficiency can be improved.

The interaction method for remote consultation provided by the present disclosure is based on the real-time audio and video cloud service interface to create a consultation group, to achieve multi-terminal information interaction based on the user datagram protocol, and the real-time audio and video cloud service may automatically allocate the optimal and smoothest transmission path in real time according to the network transmission status and load status, the user datagram protocol has a low latency, thereby ensuring a real-time interaction with high-definition audio and video during the remote consultation process, effectively promoting the realization of remote consultation.

Figure 3:
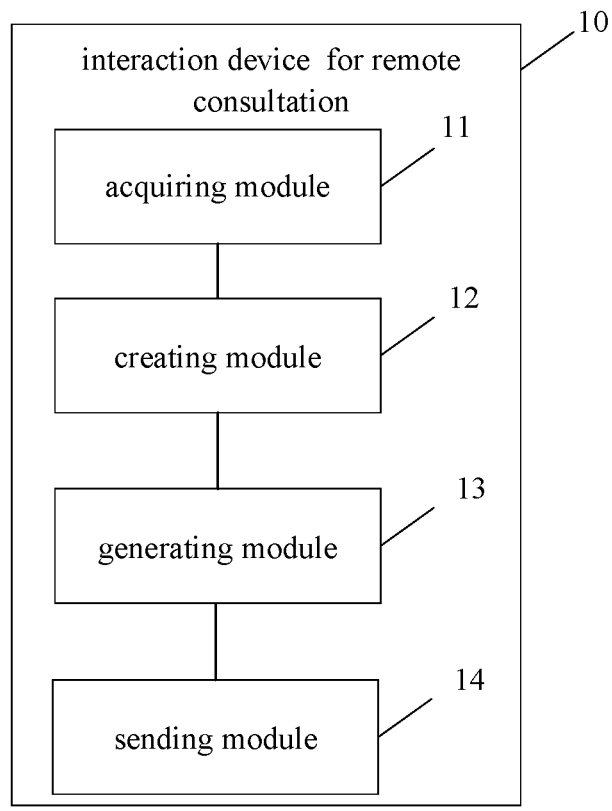
FIG. 3 is a schematic view of an interaction device for remote consultation in an embodiment of the present disclosure.

An interaction device 10 for remote consultation is further provided in some embodiments of the present disclosure. As shown in FIG. 3, the interaction device 10 for remote consultation may include: an acquiring module 11, a creating module 12, a generating module 13 and a sending module 13.

The acquiring module 11 is configured to acquire a remote consultation request.

The creating module 12 is configured to create a consultation group based on a real-time audio and video cloud service interface, and record the remote consultation request in a database.

The generating module 13 is configured to generate a consultation token based on patient information in the remote consultation request in the database and attribute information of the consultation group, and record the consultation token in the database.

The sending module 14 is configured to send the consultation token in the database to a first terminal and a second terminal, and perform an information interaction of the first terminal and the second terminal based on a user datagram protocol in response to the first terminal and the second terminal entering the consultation group according to the consultation token.

The interaction device for remote consultation provided by the present disclosure is based on the real-time audio and video cloud service interface to create a consultation group, to achieve multi-terminal information interaction based on the user datagram protocol, and the real-time audio and video cloud service may automatically allocate the optimal and smoothest transmission path in real time according to the network transmission status and load status, the user datagram protocol has a low latency, thereby ensuring a real-time interaction with high-definition audio and video during the remote consultation process, effectively promoting the realization of remote consultation.

In some embodiments of the present disclosure, the acquiring module 11 is configured to acquire the remote consultation request which is based on the user datagram protocol, and send the consultation token to the first terminal and the second terminal based on the user datagram protocol.

The sending module 14 is configured to generate a connection success notification in response to the first terminal and the second terminal entering the consultation group according to the consultation token; send the connection success notification to the first terminal and the second terminal; acquire audio and video stream information pushed by the first terminal; and send the audio and video stream information to the second terminal, based on the real-time audio and video cloud service interface and the user datagram protocol.

In some embodiments of the present disclosure, the sending module 14 is configured to: acquire the audio and video stream information which is encoded, compressed and pushed by the first terminal; send, to the second terminal, the audio and video stream information which is encoded, compressed and pushed, to enable the second terminal to decode and display the audio and video stream information which is encoded, compressed and pushed.

The interaction device for remote consultation provided by the present disclosure is based on the real-time audio and video cloud service interface to create a consultation group, to achieve multi-terminal information interaction based on the user datagram protocol, and the real-time audio and video cloud service may automatically allocate the optimal and smoothest transmission path in real time according to the network transmission status and load status, the user datagram protocol has a low latency, thereby ensuring a real-time interaction with high-definition audio and video during the remote consultation process, effectively promoting the realization of remote consultation.

An interaction device for remote consultation is further provided in some embodiments of the present disclosure, including a processor, a memory and a program, where the processor executes the program to:

acquire a remote consultation request;

create a consultation group based on a real-time audio and video cloud service interface, and record the remote consultation request in a database;

generate a consultation token based on patient information in the remote consultation request in the database and attribute information of the consultation group, and record the consultation token in the database; and send the consultation token in the database to a first terminal and a second terminal, and perform an information interaction of the first terminal and the second terminal based on a user datagram protocol in response to the first terminal and the second terminal entering the consultation group according to the consultation token.

Optionally, the processor executes the program to acquire the remote consultation request which is based on the user datagram protocol;

where the processor executes the program to send the consultation token to the first terminal and the second terminal based on the user datagram protocol.

Optionally, the processor executes the program to:

generate a connection success notification in response to the first terminal and the second terminal entering the consultation group according to the consultation token;

send the connection success notification to the first terminal and the second terminal;

acquire audio and video stream information pushed by the first terminal; and send the audio and video stream information to the second terminal, based on the real-time audio and video cloud service interface and the user datagram protocol.

Optionally, the processor executes the program to acquire the audio and video stream information which is encoded, compressed and pushed by the first terminal;

where the processor executes the program to send, to the second terminal, the audio and video stream information which is encoded, compressed and pushed, to enable the second terminal to decode and display the audio and video stream information which is encoded, compressed and pushed.

Optionally, the user datagram protocol includes a service quality policy and a packet loss compensation method, the packet loss compensation method adopts a packet loss retransmission;

the patient information includes at least one of patient identification information and registration information;

the attribute information of the consultation group includes at least one of business application account information, a name of the consultation group or a service type of the consultation group.

Optionally, the registration information includes: a consultation order, registration section information, and the business application account information include consultation business type information.

Figure 4:
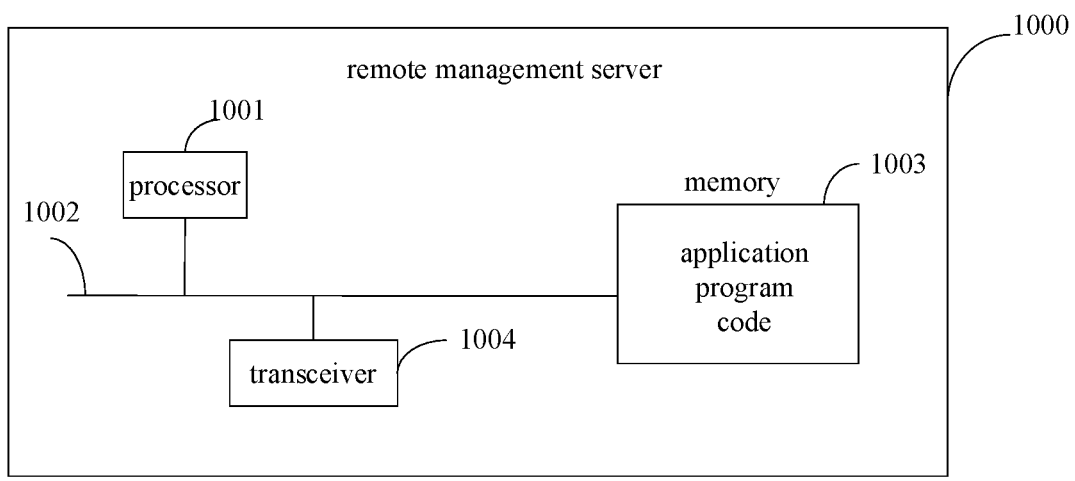
FIG. 4 is a schematic view of a remote management server in an embodiment of the present disclosure.

A remote management server is further provided in some embodiments of the present disclosure. As shown in FIG. 4, the remote management server 1000 shown in FIG. 4 includes: a processor 1001 and a memory 1003. The processor 1001 is connected to the memory 1003, for example, via the bus 1002. Optionally, the electronic device 1000 may further include a transceiver 1004. It should be noted that in practical applications, the transceiver 1004 is not limited to one, and the structure of the electronic device 1000 does not constitute a limitation on the embodiments of the present disclosure.

The processor 1001 may be a Central Processing Unit (CPU), a general-purpose processor, a Digital Signal Processor (DSP), an Application Specific Integrated Circuit (ASIC), a Field Programmable Gate Array (FPGA) or other programmable logic devices, transistor logic devices, hardware components, or any combination thereof. It can implement or execute various exemplary logical blocks, modules, and circuits described in conjunction with the disclosure of the present disclosure. The processor 1001 may also be a combination that realizes a calculation function, for example, includes one or more microprocessor combinations, a combination of a DSP and a microprocessor, and so on.

The bus 1002 may include a path to transfer information between the above components. The bus 1002 may be a Peripheral Component Interconnect (PCI) bus or an Extended Industry Standard Architecture (EISA) bus. The bus 1002 can be divided into an address bus, a data bus, and a control bus. For ease of representation, only a thick line is used in FIG. 4, but it does not mean that there is only one bus or one type of bus.

The memory 1003 may be a Read Only Memory (ROM) or other types of static storage devices that can store static information and instructions, a Random Access Memory (RAM), or other types of information and instructions that can be stored Dynamic storage devices can also be Electrically Erasable Programmable Read Only Memory (EEPROM), Compact Disc Read Only Memory (CD-ROM) or other disc storage, disc storage (including compact disc, laser Optical discs, optical discs, digital versatile discs, Blu-ray discs, etc.), magnetic disk storage media or other magnetic storage devices, or any other media that can be used to carry or store the desired program code in the form of instructions or data structures and can be accessed by a computer, but not limited to this.

The memory 1003 is configured to store application program codes for executing the solution of the present disclosure, and is controlled and executed by the processor 1001. The processor 1001 is configured to execute the application program code stored in the memory 1003 to implement the content shown in the foregoing method embodiment.

The processor 1001 executes the program to:

acquire a remote consultation request;

create a consultation group based on a real-time audio and video cloud service interface, and record the remote consultation request in a database;

generate a consultation token based on patient information in the remote consultation request in the database and attribute information of the consultation group, and record the consultation token in the database; and send the consultation token in the database to a first terminal and a second terminal, and perform an information interaction of the first terminal and the second terminal based on a user datagram protocol in response to the first terminal and the second terminal entering the consultation group according to the consultation token.

Optionally, the processor 1001 executes the program to acquire the remote consultation request which is based on the user datagram protocol;

where the processor executes the program to send the consultation token to the first terminal and the second terminal based on the user datagram protocol.

Optionally, the processor 1001 executes the program to:

generate a connection success notification in response to the first terminal and the second terminal entering the consultation group according to the consultation token;

send the connection success notification to the first terminal and the second terminal;

acquire audio and video stream information pushed by the first terminal; and send the audio and video stream information to the second terminal, based on the real-time audio and video cloud service interface and the user datagram protocol.

Optionally, the processor 1001 executes the program to acquire the audio and video stream information which is encoded, compressed and pushed by the first terminal;

where the processor executes the program to send, to the second terminal, the audio and video stream information which is encoded, compressed and pushed, to enable the second terminal to decode and display the audio and video stream information which is encoded, compressed and pushed.

Optionally, the user datagram protocol includes a service quality policy and a packet loss compensation method, the packet loss compensation method adopts a packet loss retransmission;

the patient information includes at least one of patient identification information and registration information;

the attribute information of the consultation group includes at least one of business application account information, a name of the consultation group or a service type of the consultation group.

Optionally, the registration information includes: a consultation order, registration section information, and the business application account information include consultation business type information.

According to the remote management server in the embodiments of the present disclosure, it is able to achieve multi-terminal information interaction based on the user datagram protocol, and the real-time audio and video cloud service may automatically allocate the optimal and smoothest transmission path in real time according to the network transmission status and load status, the user datagram protocol has a low latency, thereby ensuring a real-time interaction with high-definition audio and video during the remote consultation process, effectively promoting the realization of remote consultation.

Figure 5:
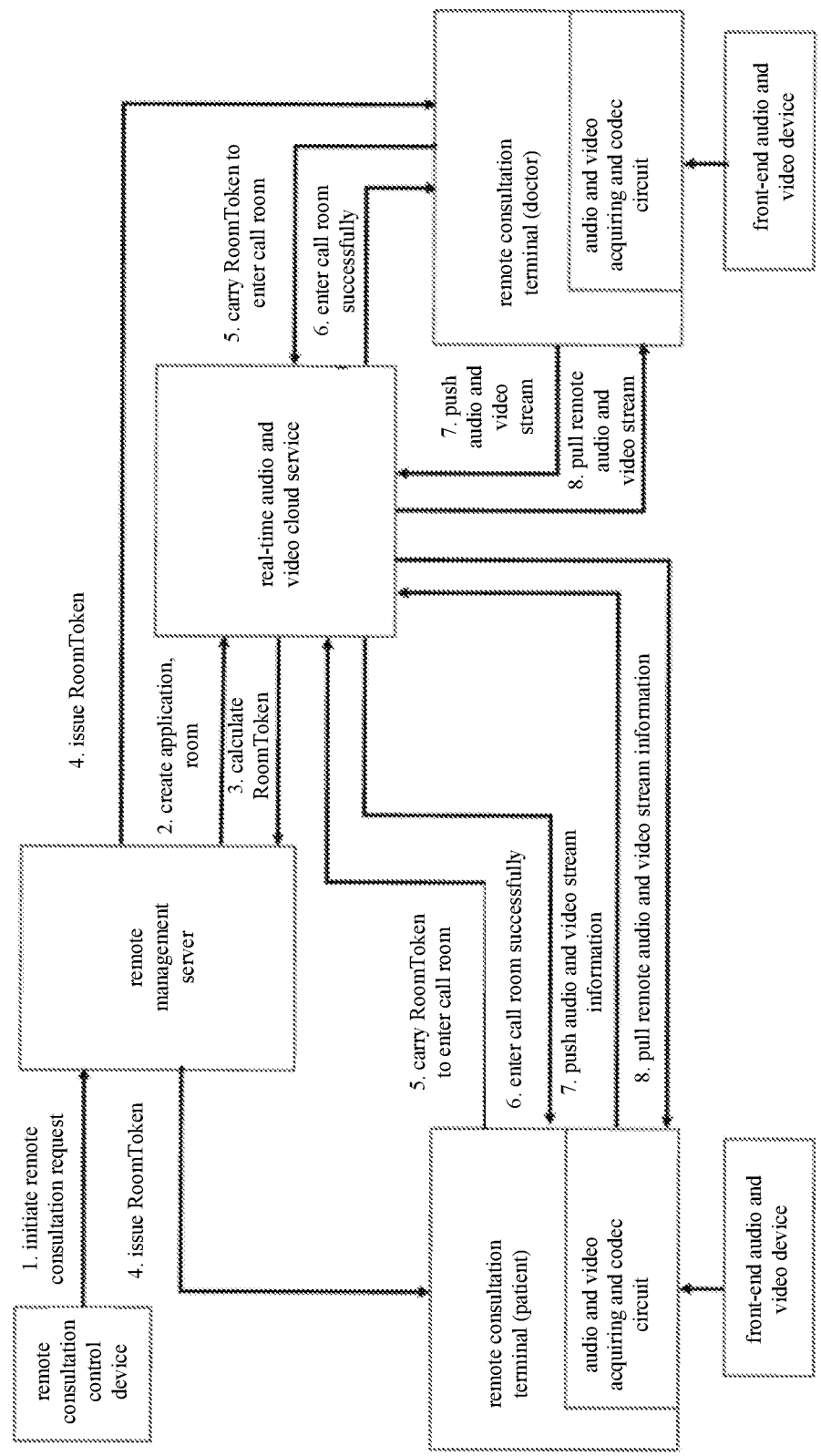
FIG. 5 is a schematic view of an interaction principle of an interaction system for remote consultation in an embodiment of the present disclosure.

An interaction system for remote consultation is provided in some embodiments of the present disclosure, as shown in FIG. 5, which includes a remote management server, a remote consultation control device, a first terminal, and a second terminal. As shown in the drawing, the first terminal is the "remote consultation terminal (patient)" in the drawing, and the second terminal is the "remote consultation terminal (doctor)" in the drawing.

The remote consultation control device is configured to send the remote consultation request to the remote management server.

The remote management server includes a real-time audio and video cloud service interface configured to: create a consultation group based on a real-time audio and video cloud service interface and the remote consultation request; generate a consultation token based on patient information in the remote consultation request in the database and the attribute information of the consultation group.

The first terminal and the second terminal are configured to receive the consultation token sent by the remote management server, enter the consultation group based on the consultation token, and exchange information based on a user datagram protocol.

According to the interaction system for remote consultation in the embodiments of the present disclosure, it is able to achieve multi-terminal information interaction based on the user datagram protocol, and the real-time audio and video cloud service may automatically allocate the optimal and smoothest transmission path in real time according to the network transmission status and load status, the user datagram protocol has a low latency, thereby ensuring a real-time interaction with high-definition audio and video during the remote consultation process, effectively promoting the realization of remote consultation.

In some embodiments of the present disclosure, as shown in FIG. 5, both the first terminal and the second terminal include an audio and video acquisition codec module, the audio and video acquiring and codec circuit is configured to encode and compress an audio and video stream acquired by the first terminal or the second terminal, and decode audio and video stream information sent by the remote management server.

A computer-readable storage medium is provided in an embodiment of the present disclosure, where a computer program is stored in the computer-readable storage medium, and the computer program is executed by a computer, to perform the above interaction method for remote consultation. Compared with the related art, the interaction method for remote consultation stored on the computer-readable storage medium provided by the present disclosure may create a consultation group based on a real-time audio and video cloud service interface, it is able to achieve multi-terminal information interaction based on the user datagram protocol, and the real-time audio and video cloud service may automatically allocate the optimal and smoothest transmission path in real time according to the network transmission status and load status, the user datagram protocol has a low latency, thereby ensuring a real-time interaction with high-definition audio and video during the remote consultation process, effectively promoting the realization of remote consultation.

In order to facilitate the understanding of the technical solution of the present disclosure, the application examples are illustrated with FIG. 5 and the actual application scenario:

On the remote consultation control device of the hospital, such as a registration device, the first step is to initiate a remote consultation request, which is received by the remote management server, and the remote management server is connected to the real-time audio and video cloud service through the real-time audio and video cloud service interface, and calculates Room Token (that is, consultation token) through the real-time audio and video cloud service. The consultation token is generated by the remote management service area, and the consultation token is issued and transmitted to the remote consultation terminal including the first terminal and the second terminal corresponding to the remote consultation terminal (patient) and the remote consultation terminal (doctor) in the figure. The two remote consultation terminals carry consultation tokens and join the call room through the real-time audio and video cloud service, that is, participate in the consultation group previously constructed by the remote management server. The remote management server detects that all the remote consultation terminals have entered the consultation group through the real-time audio and video cloud service, and feeds back the notification of the successful joining of the call room to the remote consultation terminal. The connection of the above system modules can be based on the user datagram protocol to ensure the real-time nature of the remote consultation. The real-time audio and video cloud service can automatically allocate the optimal and smoothest transmission according to the network transmission status and load status. The characteristics of the path can also ensure real-time interaction with high-definition audio and video during the remote consultation. Of course, in practice, there are also front-end audio and video devices, such as displays, cameras, and microphones, which are connected to remote consultation terminals to collect and play information. The numbers in FIG. 5 indicate the sequence of steps in a reference case.

It should be understood that although the steps in the flowchart in the drawings are displayed in order according to the arrows, the steps are not necessarily executed in the order indicated by the arrows. Unless there is a clear description in this article, the execution of these steps is not strictly limited in order, and they can be executed in other orders. Moreover, at least a part of the steps in the flowchart of the drawings may include multiple sub-steps or multiple stages. These sub-steps or stages are not necessarily executed at the same time, but may be executed at different times, and the order of execution is also It is not necessarily carried out sequentially, but may be executed in turn or alternately with at least a part of other steps or sub-steps or stages of other steps.

The above is only a part of the embodiments of the present disclosure. It should be noted that for those of ordinary skill in the art, without departing from the principles of the present disclosure, several improvements and retouches can be made. These improvements and retouches should also be regarded as the scope of the present disclosure.

What is claimed is:

1. An interaction method for remote consultation, comprising:
    acquiring a remote consultation request;
    creating a consultation group based on a real-time audio and video cloud service interface, and recording the remote consultation request in a database;
    generating a consultation token based on patient information in the remote consultation request in the database and attribute information of the consultation group, and recording the consultation token in the database; and
    sending the consultation token in the database to a first terminal and a second terminal, and performing an information interaction by the first terminal and the second terminal based on a user datagram protocol in response to the first terminal and the second terminal entering the consultation group according to the consultation token.

2. The interaction method for remote consultation according to claim 1, wherein the acquiring the remote consultation request comprises:
    acquiring the remote consultation request which is based on the user datagram protocol; and
    the sending the consultation token in the database to the first terminal and the second terminal comprises:
    sending the consultation token to the first terminal and the second terminal based on the user datagram protocol.

3. The interaction method for remote consultation according to claim 1, wherein the performing the information interaction by the first terminal and the second terminal based on the user datagram protocol in response to the first terminal and the second terminal entering the consultation group according to the consultation token comprises:
    generating a connection success notification in response to the first terminal and the second terminal entering the consultation group according to the consultation token;
    sending the connection success notification to the first terminal and the second terminal;
    acquiring audio and video stream information pushed by the first terminal; and
    sending the audio and video stream information to the second terminal, based on the real-time audio and video cloud service interface and the user datagram protocol.

4. The interaction method for remote consultation according to claim 3, wherein the acquiring the audio and video stream information pushed by the first terminal comprises:
    acquiring the audio and video stream information which is encoded, compressed and pushed by the first terminal; and
    the sending the audio and video stream information to the second terminal based on the real-time audio and video cloud service interface and the user datagram protocol comprises:
    sending, to the second terminal, the audio and video stream information which is encoded, compressed and pushed, to enable the second terminal to decode and display the audio and video stream information which is encoded, compressed and pushed.

5. The interaction method for remote consultation according to claim 1, wherein the user datagram protocol comprises a service quality policy and a packet loss compensation method, the packet loss compensation method adopts a packet loss retransmission;
    the patient information comprises at least one of patient identification information and registration information;
    the attribute information of the consultation group comprises at least one of business application account information, a consultation group name or a consultation group service type.

6. The interaction method for remote consultation according to claim 5, wherein the registration information comprises: a consultation order, registration section information, and the business application account information comprises consultation business type information.

7. The interaction method for remote consultation according to claim 3, wherein the first terminal is a terminal of a patient, and the second terminal is a terminal of a doctor;
    wherein the second terminal comprises a plurality of sub terminals, and each of the sub terminals corresponds to a doctor;
    the sending the audio and video stream information to the second terminal based on the real-time audio and video cloud service interface and the user datagram protocol comprises:
    sending the audio and video stream information to the sub terminals of the second terminal based on the real-time audio and video cloud service interface and the user datagram protocol, to enable the patient to exchange information with a plurality of doctors.

8. An interaction device for remote consultation, comprising a processor, a memory and a program, wherein the processor executes the program to:
    acquire a remote consultation request;
    create a consultation group based on a real-time audio and video cloud service interface, and record the remote consultation request in a database;
    generate a consultation token based on patient information in the remote consultation request in the database and attribute information of the consultation group, and record the consultation token in the database; and send the consultation token in the database to a first terminal and a second terminal, and perform an information interaction of the first terminal and the second terminal based on a user datagram protocol in response to the first terminal and the second terminal entering the consultation group according to the consultation token.

9. The interaction device for remote consultation according to claim 8, wherein the processor executes the program to acquire the remote consultation request which is based on the user datagram protocol;

wherein the processor executes the program to send the consultation token to the first terminal and the second terminal based on the user datagram protocol.

10. The interaction device for remote consultation according to claim 8, wherein the processor executes the program to:

generate a connection success notification in response to the first terminal and the second terminal entering the consultation group according to the consultation token;

send the connection success notification to the first terminal and the second terminal;

acquire audio and video stream information pushed by the first terminal; and send the audio and video stream information to the second terminal, based on the real-time audio and video cloud service interface and the user datagram protocol.

11. The interaction device for remote consultation according to claim 10, wherein the processor executes the program to acquire the audio and video stream information which is encoded, compressed and pushed by the first terminal;

wherein the processor executes the program to send, to the second terminal, the audio and video stream information which is encoded, compressed and pushed, to enable the second terminal to decode and display the audio and video stream information which is encoded, compressed and pushed.

12. The interaction device for remote consultation according to claim 8, wherein the user datagram protocol comprises a service quality policy and a packet loss compensation method, the packet loss compensation method adopts a packet loss retransmission;

the patient information comprises at least one of patient identification information and registration information;

the attribute information of the consultation group comprises at least one of business application account information, a name of the consultation group or a service type of the consultation group.

13. The interaction device for remote consultation according to claim 12, wherein the registration information comprises: a consultation order, registration section information, and the business application account information comprises consultation business type information.

14. An interaction system for remote consultation, comprising a remote management server, a remote consultation control device, a first terminal and a second terminal;

the remote consultation control device is configured to send a remote consultation request to the remote management server;

the remote management server comprises a real-time audio and video cloud service interface and is configured to:

create a consultation group based on a real-time audio and video cloud service interface and the remote consultation request, and record the remote consultation request in a database;

generate a consultation token based on patient information in the remote consultation request in the database and the attribute information of the consultation group, and record the consultation token in the database;

the first terminal and the second terminal are configured to receive the consultation token sent by the remote management server, enter the consultation group based on the consultation token, and exchange information based on a user datagram protocol.

15. The interaction system for remote consultation according to claim 14, wherein both the first terminal and the second terminal comprises an audio and video acquiring and codec circuit;

the audio and video acquiring and codec circuit is configured to encode and compress an audio and video stream acquired by the first terminal or the second terminal, and decode audio and video stream information sent by the remote management server.

\* \* \* \* \*